United States Patent [19]

Miura et al.

[11] E Patent Number: Re. 33,367

[45] Reissued Date of Patent: Oct. 2, 1990

[54] POLYETHER POLYMER OR COPOLYMER, MONOMER THEREFOR, AND PROCESS FOR PRODUCTION THEREOF

[75] Inventors: Katsuhito Miura, Amagasaki; Tetsuya Nakata, Ibaraki, both of Japan

[73] Assignee: Osaka Soda Co., Ltd., Osaka, Japan

[21] Appl. No.: 204,563

[22] Filed: Jun. 9, 1988

Related U.S. Patent Documents

Reissue of:

[64] Patent No.: 4,711,950
Issued: Dec. 8, 1987
Appl. No.: 925,270
Filed: Oct. 31, 1986

[30] Foreign Application Priority Data

Nov. 5, 1985 [JP] Japan ..... 60-247712
Dec. 10, 1985 [JP] Japan ..... 60-278560
Jan. 20, 1986 [JP] Japan ..... 61-10763

[51] Int. Cl.[5] ..... C08G 59/02; C08G 59/32

[52] U.S. Cl. ..... 528/409; 528/418; 549/554; 549/555

[58] Field of Search ..... 528/409, 418; 549/555

[56] References Cited

U.S. PATENT DOCUMENTS 2,996,551 8/1961 Groote ..... 549/559
3,026,216 3/1962 Sookne ..... 549/555
3,297,783 1/1967 Bailey ..... 528/418
4,711,950 12/1987 Miura et al. ..... 528/409

FOREIGN PATENT DOCUMENTS 1570547 3/1965 Fed. Rep. of Germany .

*Primary Examiner*—John Kight, III
*Assistant Examiner*—Frederick Krass
*Attorney, Agent, or Firm*—Sherman and Shalloway

[57] ABSTRACT

A polyether polymer or copolymer with a pendant group of the formula in its molecule, said polymer or copolymer consisting essentially of (1) 1 to 100 mole % of recurring units represented by the following formula (I)

(I)

and (2) 0 to 99 mole % of at least one type of recurring units represented by the following formula (II)

(II)

and having a reduced vicsocisty $\eta_{red}$, determined at 45° C. in its 0.1% benzene solution or at 80° C. in its 0.1% monochlorobenzene solution, of at least 0.01; a process for producing thereof and novel epoxyether compound therefor.

7 Claims, 5 Drawing Sheets

POLYETHER POLYMER OR COPOLYMER, MONOMER THEREFOR, AND PROCESS FOR PRODUCTION THEREOF

Matter enclosed in heavy brackets [ ] appears in the original patent but forms no part of this reissue specification; matter printed in italics indicates the additions made by reissue.

This invention relates to a novel polyether polymer or copolymer of the type in which a side chain having an oxirane group is pendant from a main chain having a polyether structure, a novel monomer used in the production of the polyether polymer or copolymer, and to processes for producing the polyether polymer or copolymer and the monomer. Particularly, this invention relates to a solvent-soluble polyether polymer or copolymer with a pendant group of the formula

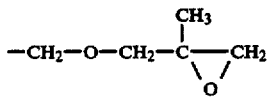

in its molecule, a novel monomer used in its production, and to a process for producing the polyether polymer or copolymer. The polymer or copolymer is useful, for example, as an epoxy resin, a rubber or elastomeric material, an adhesive, a paint, and a reactive polymer intermediate.

More specifically, this invention pertains to a polyether polymer or copolymer with a pendant group of the formula

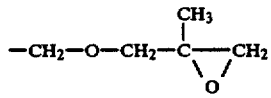

in its molecule, said polymer or copolymer consisting essentially of (1) 1 to 100 mole % of recurring units represented by the following formula (I)

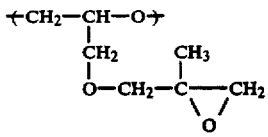

(I)

and (2) 0 to 99 mole % of at least one type of recurring units represented by the following formula (II)

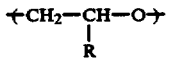

(II)

wherein R represents a member selected from the class consisting of a hydrogen atom, substituted or unsubstituted $C_1$-$C_{18}$ alkyl groups, substituted or unsubstituted $C_2$-$C_{18}$ alkenyl groups, substituted or unsubstituted $C_3$-$C_8$ cycloalkyl groups and substituted or unsubstituted $C_6$-$C_{14}$ arylgroups, and having a reduced viscosity $\eta_{red}$, determined at 45° C. in its 0.1% benzene solution or at 80° C. in its 0.1% monochlorobenzene solution, of at least 0.01.

This invention also pertains to processes for producing the polyether polymer or copolymer and the monomer of formula (I-a).

Various difunctional or 2,3-epoxypropyl-2',3'-epoxy-2'-methylpropyl ether represented by the following formula (I-a)

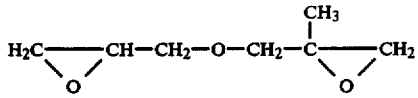

(I-a)

which is not described in the known literature, and which is useful for producing a polymer composed of the recurring units of formula (I) or a copolymer comprising the recurring units of formula (I).

This invention further pertains to higher oxirane compounds have been known and used in various applications. For example diglycidyl ether of the following formula

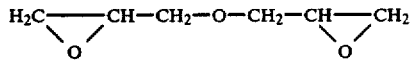

is known as a compound closest to the compound of formula (I-a). Furthermore, diglycidyl ethers of bisphenols are known as epoxy resins. The two oxirane rings of these compounds have quite the same reactivity, and it is difficult to expect reaction of only one oxirane ring.

Compounds having two or more oxirane rings having different reactivities are known. For example, there is known vinylcyclohexene diepoxide of the following formula

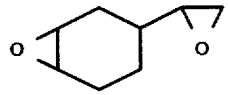

having two oxirane groups. It is difficult however to perform ring-opening polymerization of only one of these oxirane rings completely selectively.

Generally, in the polymerization of a monomer containing two or more groups having similar polymerizabilities as functional groups as in the above difunctional or higher oxirane compounds, crosslinking reaction occurs and the formation of an insoluble gelled product cannot be avoided. Accordingly, it is virtually impossible to obtain a high-molecular-weight polymer while keeping one of two functional groups, for example, still reactive. Hence, to obtain a polymer or copolymer having an oxirane group in a side chain, there has been exclusively used a method which comprises polymerizing a monomer having a vinyl polymerizable functional group and an oxirane group which have quite different reactivities, for example glycidyl methacrylate, in the presence of a radical initiator such as a peroxide.

It has previously been known to synthesize a polymer having a main chain of a polyether structure by ring-opening polymerization of an oxirane compound. There has been no example known heretofore in which a solvent-soluble polyether polymer or copolymer of high molecular weight is obtained by ring-opening polymerization of a difunctional oxirane compound to polymerize one oxirane ring selectively while leaving the other oxirane ring unpolymerized as a side chain. Polymers or copolymers having an oxirane functional group in a side chain have attracted attention because various functions are expected owing to the presence of the oxirane functional group. Various attempts have been made in the past to polymerize monomers having functional groups.

The present invention have made investigations in order to develop a difunctional oxirane compound of a new type which serves to realize such expectation. These investigations have led to the discovery that a difunctional oxirane compound of the following formula (I-a)

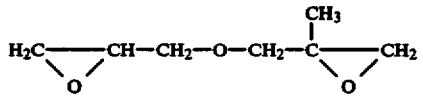

(I-a)

which is not described in the prior literature can be easily synthesized, and the present inventors have succeeded in synthesizing it. The inventors have also found the compound of formula (I-a) to have unique reaction specificity in that the oxirane ring on the left end of the formula participates very selectively in its ringopening polymerization by a polymerization catalyst in accordance with this invention which is described hereinafter, but the oxirane ring having a methyl substituent on the right end does not participate in the reaction but remains unchanged, and that no crosslinking reaction occurs in spite of its difunctionality. It has further been found that because of this reaction specificity, the novel difunctional oxirane compound of formula (I-a) does not form a solvent-insoluble gelled product by crosslinking reaction, and by the ring-opening polymerization catalyst in accordance with this invention, it can give a novel solvent-soluble reactive polyether polymer or copolymer of the type in which a group of the formula

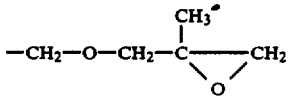

is pendant from a main chain of the polyether structure, and that the resulting polyether polymer or copolymer is very useful in such applications as an epoxy resin, a rubber or elastomeric material, an adhesive, a paint and a reactive polymer intermediate.

It is an object of this invention therefore to provide a novel polyether polymer or copolymer with a pendant group of the formula

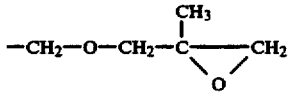

in its molecule, a novel difunctional oxirane compound used in the production of the polymer or copolymer, and processes for producing the polymer or copolymer and the difunctional oxirane compounds.

The above and other objects of this invention along with its advantages will become more apparent from the following description and accompanying drawings in which:

Figure 1:
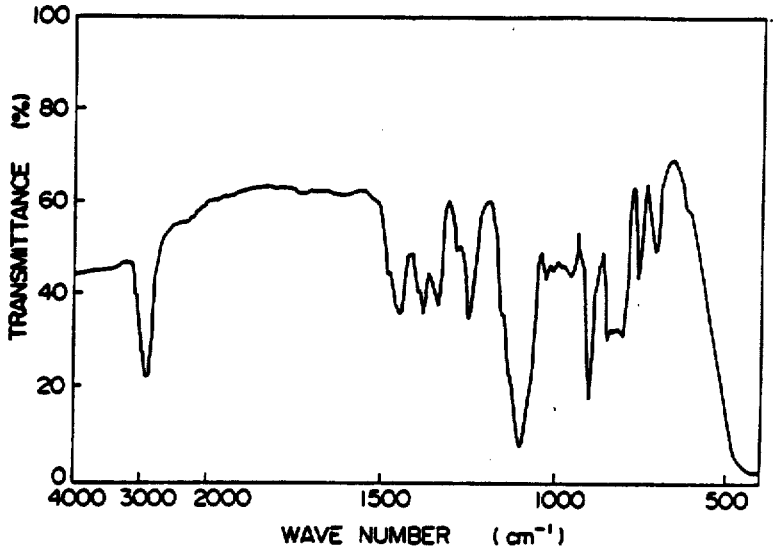
FIG. 1 is a plot of the infrared absorption spectrum of the compound of formula (I-a) produced in Example 1.

The difunctional oxirane compound of this invention, 2,3-epoxypropyl-2',3'-epoxy-2'-methylpropyl ether of the following formula (I-a)

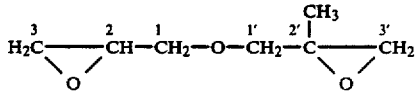

(I-a)

can be synthesized by properly selecting ether synthesizing means and oxirane ring forming means known per se.

In one embodiment, the compound of formula (I-a) can be synthesized by epoxidizing a known compound, allyl methallyl ether of the formula

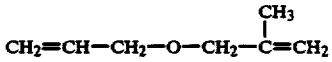

(I-b)

with an oxidizing agent such as hydrogen peroxide or a peroxy acid. When hydrogen peroxide is used in this embodiment, the compound of formula (I-a) can be formed by contacting allyl methallyl ether with hydrogen peroxide in the presence of a weakly alkaline substance such as potassium hydrogen carbonate and a nitrile compound such as acetonitrile, optionally using a solvent such as methanol, to epoxidize allyl methallyl ether. Alternatively, the compound of formula (I-a) can be formed by contacting allyl methallyl ether with hydrogen peroxide in the presence of a catalyst, for example a compound of a metal such as selenium, tungsten, or molybdenum (e.g., selenium dioxide, a tungstic acid or a molybdic acid) to epoxidize allyl methallyl ether.

In the practice of the first-mentioned epoxidization reaction, the amount of the weakly alkaline substance can be properly varied, but is, for example, about 0.1 to 1 part by weight per part by weight of allyl methallyl ether. The amount of the nitrile compound used can also be properly varied. It is, for example, about 1 to 10 moles per mole of the allyl methallyl ether. The amount of the solvent used can also be varied properly, and is, for example, about 0 to 10 parts by weight per part by weight of allyl methallyl ether. The reaction temperature and time can also be properly varied. For example, the reaction temperature is about 10° to 70° C., and the reaction time is about 0.5 to 50 hours. The concentration and amount of hydrogen peroxide can also be varied properly. For example, an aqueous solution of hydrogen peroxide having a concentration of about 10 to 60% by weight is used in an amount of about 1 to 10 moles per mole of allyl methallyl ether.

In the practice of the latter epoxidization reaction, the amount of the metallic compound catalyst can be properly chosen, and is, for example, about 0.001 to 0.1 mole per mole of allyl methallyl ether. The reaction temperature and time can also be properly varied. For example, the reaction temperature is about 20° to 90° C., and the reaction time is about 0.5 to 50 hours. The concentration and amount of hydrogen peroxide can also be varied properly. For example, an aqueous solution of hydrogen peroxide having a concentration of about 10 to 60% by weight is used in an amount of about 0.1 to 10 moles per mole of allyl methallyl ether.

When the peroxy acid is used in the above embodiment, the compound of formula (I-a) can be obtained by contacting allyl methallyl ether with the peroxy acid in the presence or absence of a solvent such as tetrahydrofuran, diethyl ether or methylene chloride to epoxidize it. Examples of the peroxy acid used include organic peroxy acids such as peroxyacetic acid, peroxybenzoic acid, and peroxyformic acid. The amount of the peroxy acid can be varied properly, and is, for example, about 1 to 10 moles per mole of allyl methallyl ether. The amount of the solvent used can be varied properly, and is, for example, about 0 to 100 parts by weight per part by weight of allyl methallyl ether. The reaction temperature and time can also be suitably selected. The reaction temperature is, for example, about 0° to 60° C., and the reaction time is about 1 to 100 hours.

In another embodiment, the compound of formula (I-a) can be synthesized by utilizing a halohydrin method known per se. In this embodiment, the compound of formula (I-a) can be synthesized by contacting a suspension of allyl methallyl ether in water with a halogen such as bromine or chlorine to form a halohydrin compound, and reacting the halohydrin compound with a suitable base such as slaked lime and sodium hydroxide to perform ring-forming reaction. In the practice of this embodiment, the amount of water used in the halohydrin-forming reaction can be selected properly, and is, for example, about 10 to 1,000 parts by weight per part by weight of allyl methallyl ether. The amount of the halogen can also be properly varied, and is, for example, about 1 to 10 moles per mole of allyl methallyl ether. The reaction temperature and time can also be varied properly. For example, the reaction temperature is about 10° to 80° C., and the reaction time is about 0.5 to 50 hours. In the epoxidization reaction of the resulting halohydrin compound, the amount of the base used can be properly chosen, and is, for example, about 1 to 10 moles per mole of allyl methallyl ether. The reaction temperature and time can also be properly chosen. For example, the reaction temperature is about 10° to 100° C., and the reaction time is about 0.5 to about 70 hours.

According to still another embodiment, the compound of formula (I-a) can be produced by a method which does not go through the form of (I-b). In this embodiment, the compound of formula (I-a) can be obtained by etherifying a mixture of a suitable combination of an epihalohydrin with an alcohol, for example a combination of epichlorohydrin and beta-methyl allyl alcohol or a combination of beta-methylepichlorohydrin and allyl alcohol, using a phase transfer catalyst such as a quaternary ammonium salt or a crown ether and a suitable base such as sodium hydroxide or potassium hydroxide in the presence or absence of a solvent such as dimethylformamide, and epoxidizing the resulting ether compound. In the practice of this embodiment, the amount of the base used in the etherification reaction can be properly varied, and is, for example, about 0.5 to 5 moles per mole of the halohydrin compound. The amount of the catalyst used can also be varied properly, and is, for example, about 0.001 to 0.1 mole per mole of the halohydrin compound. The amount of the alcohol can also be suitably varied, and is, for example, about 0.1 to 10 moles per mole of the halodydrin compound. The amount of the solvent which may be used can be varied properly, and is, for example, about 0 to 100 parts by weight per part by weight of the halohydrin compound. The reaction temperature and time can also be properly chosen. For example, the reaction temperature is about 10° to 80° C., and the reaction time is about 0.5 to 50 hours. The epoxidiation of the ether compound obtained by this reaction can be carried out also by the aforesaid methods, for example by using hydrogen peroxide or a peroxy acid, or by the reaction of forming a halohydrin compound.

The compound of formula (I-a) which is not described in the prior literature and can be obtained as described above in detail has in its molecule two reactive oxirane rings having different reactivities. The compound (I-a) can be used in various applications, for example as an intermediate for organic syntheses, a monomer for ring-operated polymerization, a monomer for crosslinking, a reactive plasticizer, a material for epoxy resins, an adhesive, a paint and a surface-treating agent.

According to this invention, the use of the compound of formula (I-a) can lead to a polyether polymer or copolymer with a pendant group of [th] *the* formula

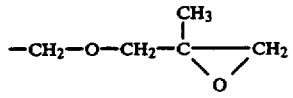

in its molecule and having a reduced viscosity $\eta_{red}$, determined at 45° C. in its 0.1% benzene solution or at 80° C. in its 0.1% monochlorobenzene solution, of at least 0.01.

In the present invention, the reduced viscosity $\eta_{red}$ of the polymer or copolymer is measured by the following method.

As a solvent, benzene is used for the homopolymer and a copolymer with propylene oxide or other copolymers, which are easily soluble in it, and monochlorobenzene is used for copolymers difficulty soluble in benzene, [or] *for* example a copolymer with epichlorohydrin. The homopolymer or the copolymer is dissolved in a concentration of 0.1% in a benzene or monochlorobenzene solution containing 0.1% of 2,2'-methylenebis(4-methyl-6-t-butylphenol). Using the solution, the reduced viscosity of the polymer or copolymer is measured by means of an Ubbelohde viscometer at 45° C. for the benzene solution and 80° C. for the monochlorobenzene solution.

The novel polyether polymer or copolymer consists essentially of (1) 1 to [10] *100* mole % of [a] recurring units represented by the following formula (I)

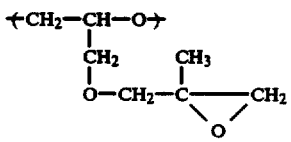

(I)

(2) 0 to 99 mole % of at least one type of recurring units represented by the following formula (II)

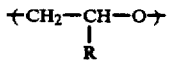

(II)

wherein R represents a member selected from the class consisting of a hydrogen atom, substituted or unsubstituted $C_1$–$C_{18}$ alkyl groups, substituted or unsubstituted $C_2$–$C_{18}$ alkenyl groups, substituted or unsubstituted $C_3$–$C_8$ cycloalkyl groups and substituted or unsubstituted $C_6$–$C_{14}$ aryl groups, and has a reduced viscosity $\eta_{red}$, determined at 45° C. in its 0.1% benzene solution or at 80° C. in its 0.1% monochlorobenzene solution, of at least 0.01.

The recurring units of formula (I) are derived by opening only the methyl-free oxirane ring of the two oxirane rings of the compound of formula (I-a) while the other methyl-containing oxirane ring being left unopen. The recurring units of formula (II) are derived by ring-opening of a monoepoxy compound of the following formula (III)

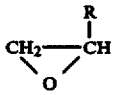

(III)

wherein R is as defined with regard to formula (II).

In the definition of R in formulae (II) or (III), examples of the $C_1$–$C_{18}$ alkyl group are methyl, ethyl, propyl, butyl, hexyl and dodecyl groups. These alkyl groups may have a substituent such as halogen, $C_1$–$C_{10}$ alkoxy, $C_2$–$C_{10}$ alkoxycarbonyl, $C_2$–$C_{10}$ acyl, $C_1$–$C_{10}$ alkylthio, and optionally substituted $C_6$–$C_{14}$ aryl. In the definition of R, examples of the $C_2$–$C_{18}$ alkenyl group are vinyl, allyl and butenyl. The alkenyl groups may have a substituent such as halogen, $C_1$–$C_{12}$ alkyl, $C_1$–$C_{10}$ alkoxy, $C_2$–$C_{10}$ alkoxycarbonyl, $C_2$–$C_{10}$ acyl and $C_1$–$C_{10}$ alkylthio. In the definition of R, [example] *examples* of the $C_3$–$C_8$ cycloalkyl group are cyclopropyl, cyclopentyl and cyclohexyl. The cycloalkyl groups may have a substituent such as halogen, $C_1$–$C_{12}$ alkyl, $C_1$–$C_{10}$ alkoxy, $C_2$–$C_{10}$ alkoxy-carbonyl, $C_2$–$C_{10}$ acyl and $C_1$–$C_{10}$ alkylthio. In the definition of R, examples of the $C_6$–$C_{14}$ aryl group are phenyl and naphthyl. The aryl groups may have a substituent such as halogen, $C_1$–$C_{12}$ alkyl, $C_1$–$C_{10}$ alkoxy, $C_2$–$C_{10}$ alkoxycarbonyl, $C_2$–$C_{10}$ acyl and $C_1$–$C_{10}$ alkylthio.

The novel polyether polymer or copolymer has a reduced viscosity $\eta_{red}$, determined at 45° C. in its 0.1% benzene solution or at 80° C. in its 0.1% monochlorobenzene solution, of at least 0.01. The polymer composed only of the recurring units of formula (I) or polymers composed substantially of the recurring units of formula (I) with less than 1 mole % [namely, the proportion of the recurring units of formula (I) exceeding 99 mole %] of the recurring units of formula (II) preferably have a reduced viscosity $\eta_{red}$, determined at 45° C. in their 0.1% benzene solution, of 0.01 to 2, particularly 0.05 to 2. Copolymers composed of 1 to 99 mole % of the recurring units of formula (I) and 99 to 1 mole % (the total 100 mole %) of the recurring units of formula (II) preferably have a reduced viscosity $\eta_{red}$, determined at 45° C. in their 0.1% benzene solution or at 80° C. in their 0.1% monochlorobenzene solution, of 0.01 to 5, especially 0.05 to 3. In the case of the copolymers, suitable mole ratios for the intended uses may be selected. For example, when the copolymers are to be used as epoxy resins, it is preferred to adjust the proportion of the recurring unit of formula (I) to at least about 30 mole %. For use as a rubberr elastomeric material, the copolymer preferably contains about 5 mole %, or amounts near it, of the recurring unit of formula (I). Such [a] preferred ranges of the proportion of the recurring units of formula (I) can be preselected and prescribed easily by experiments according to the purpose of use and the type of the recurring units of formula (II).

The novel polyether polymer or copolymer of this invention can be produced by polymerizing the compound of formula (I-a) or copolymerizing the compound of formula (I-a) and the monoepoxy compound of formula (III), in the presence of, as a catalyst, a heat-reaction product of (A) an organotin compound and (B) a complete or partial ester compound of $(HO)_3PO$ which is disclosed in U.S. Pat. No. 3,773,694 whose inventorship includes Tetsuya Nakata who is one of the coinventors of the present invention.

When, for example, the diepoxy compound of formula (I-a) in accordance with this invention is polymerized by using organoaluminum-water containing catalyst heretofore well known as a catalyst for ring-opening polymerization of a broad range of oxirane compounds, crosslinking reaction proceeds rapidly, and the solvent-soluble polyether polymer of this invention cannot be obtained.

Among the known heat-reaction products disclosed in detail in U.S. Pat. No. 3,773,694, heat-reaction products of (A) organotin compounds selected from compounds of the following formulae (i) to (iv) and (B) a complete or partial ester compound of $(HO)_3PO$ are preferably used.

$$R_a{}^1SnX_{4-atm} \qquad \text{(i)}$$

wherein $R^1$ represents a $C_1$–$C_{12}$ alkyl group, such as methyl, ethyl, propyl, hexyl and dodecyl, unsubstituted or substituted by a substituent selected from halogen, hydroxy, $C_1$–$C_{10}$ alkoxy and $C_1$–$C_{10}$ alkylthio, a $C_2$–$C_8$ alkenyl group, such as vinyl and allyl, unsubstituted or substituted by a substituent selected from halogen, hydroxy, $C_1$–$C_{10}$ alkoxy, $C_1$–$C_{10}$ alkylthio, and optionally substituted $C_6$–$C_{14}$ aryl, a $C_3$–$C_8$ cycloalkyl group, such as cyclopropyl, cyclopentyl or cyclohexyl, unsubstituted or substituted by a substituent selected from halogen, hydroxy, $C_1$–$C_{12}$ alkyl, $C_1$–$C_{10}$ alkoxy, $C_1$–$C_{10}$ alkylthio and optionally substituted $C_6$–$C_{14}$ aryl, a $C_6$–$C_{14}$ aryl group, such a phenyl and naphthyl, unsubstituted or substituted by a substituent selected from halogen, hydroxy, $C_1$–$C_{12}$ alkyl, $C_1$–$C_{10}$ alkoxy, $C_1$–$C_{10}$ alkylthio and optionally substituted $C_6$–$C_{14}$ aryl, or a $C_7$–$C_{18}$ aralkyl group, such as benzyl or phenylethyl, unsubstituted or substituted by a substituent selected from halogen, hydroxy, $C_1$–$C_{12}$ alkyl, $C_1$–$C_{10}$ alkoxy and $C_1$–$C_{10}$ alkylthio; x represents an atom or group selected from halogen atoms such as Cl, Br, I or F, $C_1$–$C_{12}$ alkoxy groups, aryloxy groups having $C_6$–$C_{18}$ aryl, acyloxy groups having $C_2$–$C_{12}$ acyl and residues of partial esters of phosphoric acid; and a is an integer of 1 to 4; provided that when a is an integer of 2 to 4, $R^1$ groups may be identical or different, and when a is 1 or 2, the X's may be identical or different.

$$R_b^1SnO_c \quad \text{(ii)}$$

wherein $R^1$ is as defined with regard to formula (i), b is 1 or 2, and when b is 1, c is 3/2 or when b is 2, c is 1, the compound of formula (ii) may form a complex with the compound of formula (i).

$$R^2\text{-}(R_2^1SnOSnR_2^1)\text{-}R_2 \quad \text{(iii)}$$

wherein $R^1$ is as defined with regard to formula (i), $R^2$ is as defined with regard to $R^1$ and X, and the two $R^2$ groups may be identical and different.

$$(R_3^3Sn)_dX' \quad \text{(iv)}$$

wherein $R^2$ is the same as defined with regard to formula (iii) provided that at least one of the three $R^2$ groups is a group selected from the groups defined for $R^1$ in formula (i); X' is a member selected from the group consisting of a carbonate group, a phosphorus or oxyacid group, a polybasic carboxylic acid group and a residual moiety of a polyhydric alcohol; and d is a number greater than 1 and corresponds to the basicity of the member X'.

Preferably, (B) is a compound represented by the following formula $$(R^3O)_3P{=}O$$

wherein $R^3$ represents a member selected from the class consisting of a hydrogen atom, $C_1$–$C_{12}$ alkyl groups $C_2$–$C_{12}$ alkenyl groups and $C_3$–$C_8$ cycloalkyl groups which may be substituted by halogen, and at least one of the $R^3$ groups represents groups other than the hydrogen atom.

In the organotin compound (a) selected from the compounds of formulae (i) to (iv), specific examples of the compounds of formula (i) are $(C_2H_5)_4Sn$, $(C_6H_5)_4Sn$, $(CH_3)_3SnF$, $(C_4H_9)_3SnCl$, $(CH_3)_3SnBr$, $(C_8H_{17})_3SnCl$, $(CH_3)_2SnF_2$, $(C_4H_9)_2SnCl_2$, $(C_{12}H_{23})_2$, (cyclo- $C_6H_{11}$ )$_2SnI_2$, $(C_4H_9)SnF_3$, $(C_8H_{17})SnCl_3$, $(C_4H_9)_3SnOC_4H_9$,

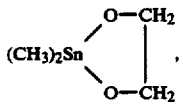

$(C_8H_{17})_3SnOCOCH_3$, $(C_8H_{17})_2Sn(OCOC_{17}H_{35})_2$, and

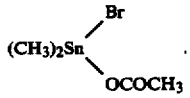

Specific examples of the compounds of formula (ii) are $(CH_3)_2SnO$, $(C_4H_9)_2SnO$, $(C_8H_{17})_2SnO$, $(C_6H_5)_2SnO$, $CH_3SnO_{3/2}$, and $C_4H_9SnO_{3/2}$.

Examples of the complex of the compound of formula (i) and the compound of formula (ii) include $(CH_3)_2SnO.(C_2H_5)_2SnBr_2$, $(CH_3)_2SnCl_2$, and $CH_2](CH_3)_2SnO]_2CH_3$ and $(CH_3)_2SnBr_2$.

Specific examples of the compounds of formula (iii) are $(CH_3)_3SnOSn(CH_3)_3$, CL $(C_4H_9)$CL, and $(CH_3COO)(C_6H_5)Sn(C_6H_5)(CH_3COO)$.

Specific examples of the compounds of formula (iv) include $[(CH_3)_3Sn]_2CO_3$, $[(C_4H_9)_3Sn]_2CO_3$, $(C_4H_9)_3SnOP(O)(OC_8H_{17})_2$, $[(C_8H_{17})_3Sn]_3PO_4$, $(C_4H_9)_3SnOCH_2CH_2OSn(C_4H_9)_3$, $(C_4H_9)_2(CH_3O)SnOCO\text{-}(CH_2)_4OCO\text{-}Sn(OCH_3)(C_4H_9)_2$, and $$\text{-}(CH_2\text{-}\underset{\underset{COOSn(C_4H_9)_3}{|}}{CH})_n\text{-}$$

Specific examples of the compounds of formula $(R^3O)_3P{=}O$ include $(C_2H_5)_3PO_4$, $(C_3H_7)_3PO_4$, $(C_4H_9)_3PO_4$, $(C_8H_{17})_3PO_4$, $(CH_2{=}CH{-}CH_2)_3PO_4$, $(C_6H_{11})_3PO_4$, $(ClCH_2{-}CH_2)_3PO_4$, $(Cl_2C_3H_5)_3PO_4$, $(C_2H_5)_2HPO_4$, $(C_4H_9)_2HPO_4$, $(C_4H_9)H_2PO_4$.

The heat-reaction product of (A) the organotin compound and (B) the complete or partial ester compound of $(HO)_3PO$ used as the catalyst can be synthesized by the means known from U.S. Pat. No. 3,773,694. For example, it can be obtained in the form of a condensation product by heating the compound (A) and the compound (B) at a temperature of about 150° to 300° C. As required, a high boiling hydrocarbon such as liquid paraffin can be used as a solvent. The ratio of the compound (A) to the compound (B) used in the formation of the heat-reaction product can be properly selected over a wide range. For example, the ratio of (A):(B), as the ratio of Sn atoms to P atoms, is from 1:10 to 10:1.

In the catalyst producing reaction, various relatively simple substances are formed and liberated by condensation reaction depending upon the types of the compounds (A) and (B). The resulting condensation product exhibits the desired activity at various degrees of condensation. The optimum degree of condensation varies depending upon the types of the compounds (A) and (B) and the ratio between them, but can be easily predetermined experimentally. Generally, the condensation product is soluble in solvents such as hexane and benzene in the early stage, but becomes insoluble as the condensation reaction proceeds.

According to this invention, there is provided a process for producing the novel polyether polymer or copolymer with a pendant group of the formula

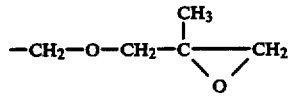

in its molecule and consisting essentially of (1) 1 to 100 mole % of recurring units of formula (I) and (2) 0 to 99 mole % of at least one type of recurring units of formula (II) and having a reduced viscosity $\eta_{red}$, determined at 45° C. in its 0.1% benzene solution or at 80° C. in its 0.1% monochlorobenzene solution, of at least 0.01, which comprises polymerizing 2,3-epoxypropyl-2',3'-epoxy-2'-methylpropyl ether of the following formula (I-a)

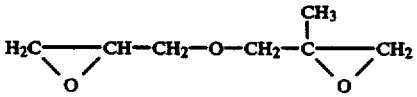

(I-a)

or copolymerizing a mixture of it with a compound of the following formula (III)

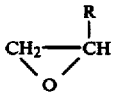

(III)

wherein R is as defined with regard to formula (II), in the presence of, as a catalyst, the above known heat-reaction product of (A) the organotin compound and (B) the complete or partial ester compound of $(HO)_3PO$.

Specific examples of the monoepoxy compound (III) used include ethylene oxide, propylene oxide, butylene oxide, butadiene monoxide, vinylcyclohexane oxide, styrene oxide, epichlorohydrin, epibromohydrin, allyl glycidyl ether, butyl glycidyl ether, phenyl glycidyl ether, naphthyl glycidyl ether, glycidyl acetate, glycidyl propionate, glycidyl benzoate, glycidyl cinnamate and glycidyl naphthonate. They may be used singly or in combination. Thus, structural units of formula (II) composed of two or more monomers above may be present in the same polymer chain in the polyether copolymer of this invention.

The polymerization or copolymerization may be carried out by contacting the compound of formula (I-a) or a mixture of it with at least one compound of formula (III) in the presence of the aforesaid heat-reaction product as a catalyst in the presence or absence of a solvent. Since the reaction proceeds even at room temperature, heating is not specially required. For example, the polymerization or copolymerization is carried out at a temperature of about 10° C. to 80° C. Preferably, the reaction is carried out with stirring or shaking. In the practice of the reaction, the presence of an unnegligible amount of water in the reaction system is inconvenient. Hence, the presence of water in the reaction system is desirably minimized.

The amount of the catalyst may be properly varied, and is, for example, about 0.01 to about 1 part by weight per 100 parts by weight of the compound of formula (I-a) or the monomeric mixture of the compound of formula (I-a) and the compound of formula (III).

The reaction pressure may be atmospheric pressure or reduced or elevated pressure, inclusive of an autogeneous pressure. Usually, pressures ranging from atmospheric pressure to 50 kg/cm$^2$ are employed.

In this invention, a solvent may be optionally present in the polymerization system. A great variety of solvents can be used in this invention. Examples include aliphatic hydrocarbons such as heptane, kerosene, n-paraffin and hexane, aromatic hydrocarbons such as benzene and toluene; halogenated hydrocarbons such as methylene chloride, chloroform, carbon tetrachloride and monochlorobenzene, ketones such as acetone and methyl ethyl ketone, ethers such as diethyl ether, di-isopropyl ether, di-n-propyl ether, di-n-butyl ether, tetrahydrofuran and dioxane, and esters such as ethyl acetate and butyl acetate.

The polyether polymer or copolymer is useful, for example, as an epoxy resin, a rubber or elastomeric material, an adhesive, a paint, or a reactive polymer intermediate.

The following examples illustrate the present invention in more detail.

EXAMPLE 1

Compound of formula (I-a)

A flask equipped with a reflux condenser, a thermometer and a stirrer was charged with 300 ml of methanol, 331 g (8.0 moles) of acetonitrile, 150 g (1.3 moles) of allyl methallyl ether and 107 g of potassium hydrogen carbonate, and with stirring at 50° C., 402 ml (3.5 moles) of a 30% by weight aqueous solution of hydrogen peroxide was added dropwise over 6 hours. After the addition, the mixture was maintained at the same temperature for 3 hours. After the reaction, the reaction mixture was cooled, and 500 ml of cold water was added. The mixture was extracted with five 150 ml portions of methylene chloride, three 100 ml portions of water, three 100 ml portions of water, dried over sodium sulfate, and distilled under reduced pressure to give 160 g (yield 83%) of 2,3-epoxypropyl-2',3'-epoxy-2'-methylpropyl ether.

The properties and NMR spectral data of the product are shown below.

Physical properties bp: 85° C./8 mm Hg $d_4^{25}$: 1.069

$n_D^{25}$: 1.4396

Assignment of NMR spectrum

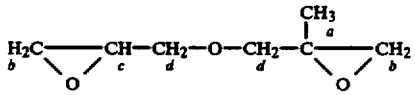

Solvent: $CDCl_3$; internal standard TMS δ:

| | |
|---|---|
| 1.35 | (3H, s, a) |
| 2.45–2.90 | (4H, m, b) |
| 2.90–3.35 | (1H, m, c) |
| 3.35–4.15 | (4H, m, d). |

The infrared absorption spectrum of the resulting product is shown in FIG. 1.

EXAMPLE 2

A three-necked flask equipped with a stirrer, a thermometer and a distillation device was charged with 12.5 g of dibutyltin oxide and 26.6 g of tributyl phosphate. With stirring in a stream of nitrogen, the compounds were heated at 250° C. for 20 minutes, and the distillate was removed. A solid condensation product was obtained was a residue.

The inside of the 50 ml glass ampoule was purged with nitrogen, and the ampoule was charged with 40 mg of the condensation product obtained as above and 15 g of 2,3-epoxypropyl-2',3'-epoxy-2'-methylpropyl ether having a concentration of less than 10 ppm, and the ampoule was sealed up. With shaking, the compound [as] *was* reacted at 40° C. for 48 hours. After the reaction, the reaction mixture was poured into 100 ml of hexane containing 0.5 % by weight of 2,2'-methylenebis(4-methyl-6-t-butylphenol), and immersed overnight. Hexane was then removed by decantation, and the residue was washed twice with 100 ml of the same hexane as used above, and then dried to give 12.7 g (yield 85%) of a polymer. The polymer had a reduced viscosity, measured at 45° C. in its 0.1% benzene solution, of 0.45 and an epoxy equivalent of 142 (theory 144).

Figure 2:
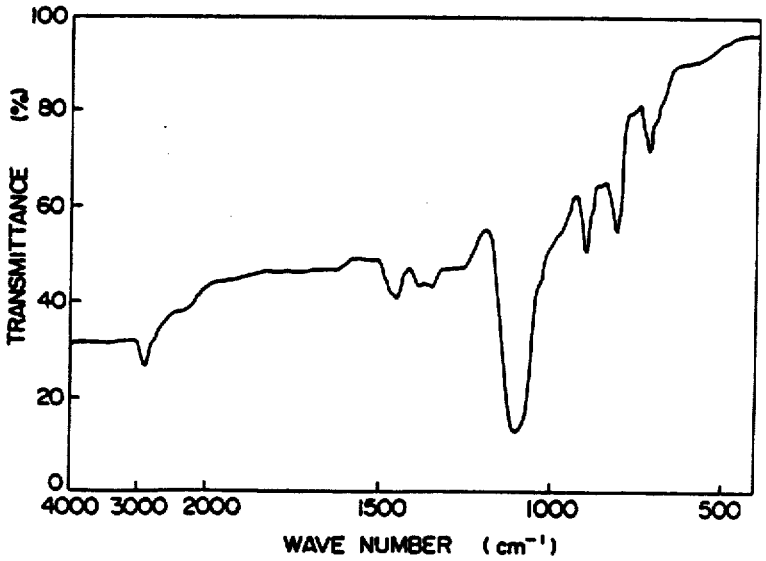
FIG. 2 is a plot of the infrared absorption spectrum of the polymer of the compound of formula (I-a) produced in Example 2.
Figure 3:
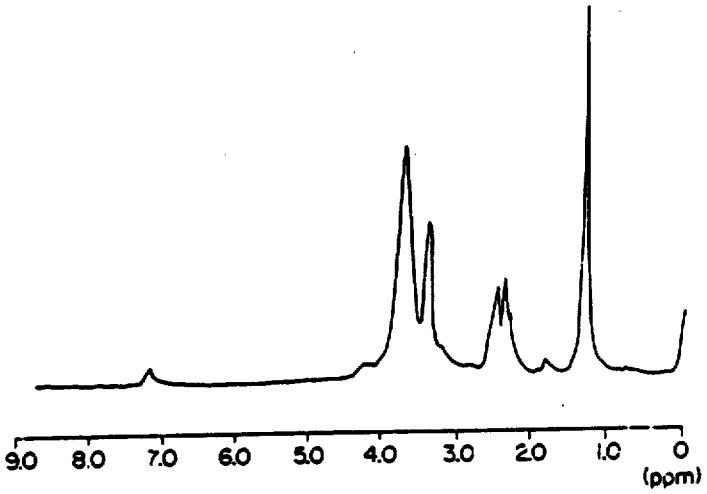
FIG. 3 is a plot of the nuclear magnetic resonance spectrum of the polymer produced in Example 2.

The infrared absorption spectrum of the polymer is shown in FIG. 2, and the nuclear magnetic resonance spectrum, in FIG. 3.

EXAMPLE 3

Tributyltin chloride (10.5 g) and 17.4 g of tributyl phosphate were put in the same flask as used in Example 2. With stirring in a stream of nitrogen, the mixture was heated at 250° C. for 30 minutes, and the distillate was removed. A solid condensation product was obtained as a residue.

The same polymerization as in Example 2 was carried out except that 25 mg of the resulting condensation product was used as the catalyt and the polymerization was carried out at 80° C. for 6 hours. There was obtained 12.2 g (yield 81%) of a polymer having a reduced viscosity, determined at 45° C. in its 0.1% benzene solution, of 0.09 and an epoxy equivalent of 143.

EXAMPLE 4

Diphenyltin dichloride (11.0 g) and 16.9 g of tributyl phosphate were put in the same flask as used in Example 2. With stirring in a stream of nitrogen, the mixture was heated at 250° C. for 35 minutes, and the distillate was removed. A solid condensation product was obtained as a residue.

The same polymerization as in Example 2 was carried out except that 25 mg of the resulting condensation product was used as the catalyst and the polymerization was carried out at 30° C. for 60 hours. There was obtained 11.8 g (yield 79%) of a polymer having a reduced viscosity, determined at 45° C. in its 0.1% benzene solution, of 0.92 and an epoxy equivalent of 145.

EXAMPLE 5

Dibutyltin oxide (10.0 g) and 23.4 g of tributyl phosphate were fed into a three-necked flask equipped with a stirrer, a thermometer and a distillation device. With stirring in a stream of nitrogen, they were heated at 260° C. for 15 minutes, and the distillate was removed. A solid condensation product was obtained as a residue.

The inside of a 50 ml glass ampoule was purged with nitrogen, and 30 mg of the condensation product, a mixture of 12 g of 2,3-epoxypropyl-2',3'-epoxy-2'-methyl-propyl ether and 20 g of propylene oxide having a water content of less than 10 ppm were charged into it. The ampoule was sealed up, and with shaking, the mixture was maintained at 40° C. for 50 hours. After the reaction, the reaction mixture was put into 100 ml of methanol containing 0.5% by weight of 2,2'-methylenebis(4-methyl-6-t-butylphenol) and immersed overnight. Methanol was removed by decantation, and the residue was washed twice with 100 ml of methanol and then dried under reduced pressure at 100° C. for 8 hours to give 29 g of a tacky rubbery polymer.

The mole ratios of the monomers charged, the reaction conditions, and the composition of the resulting copolymer are shown in Table 1.

Figure 4:
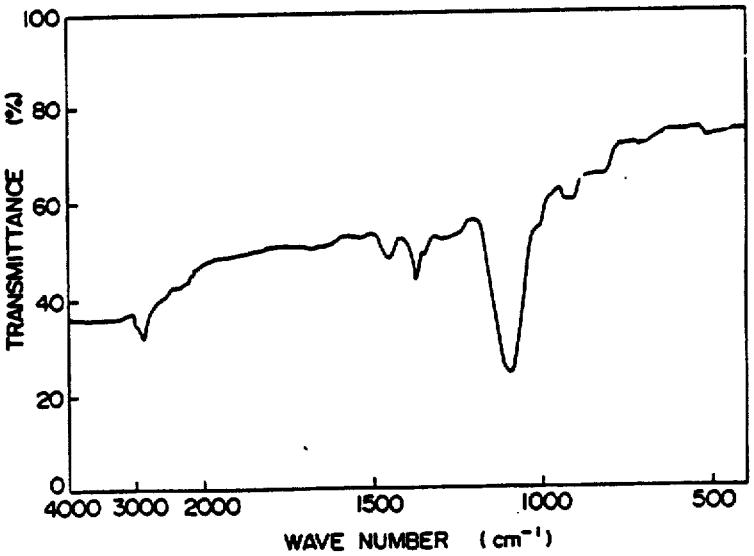
FIG. 4 is a plot of the infrared absorption spectrum of the copolymer produced in Example 5.
Figure 5:
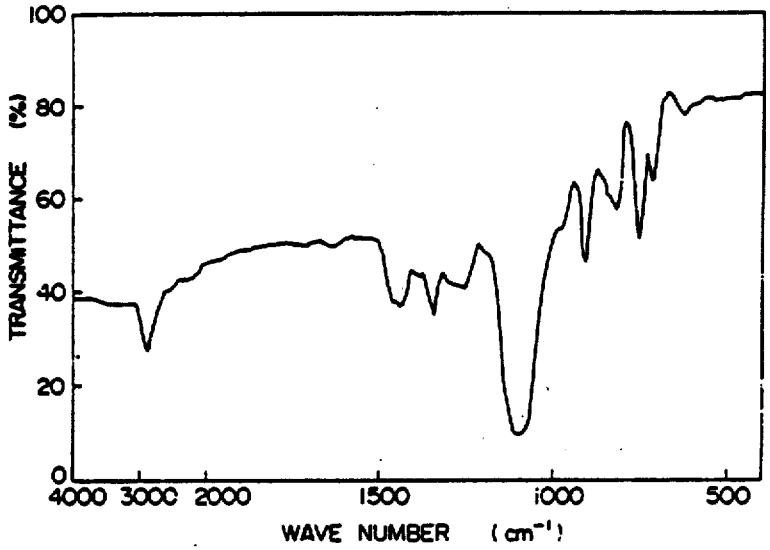
FIGS. 5 to 8 are plots of the copolymers obtained in Examples 6 to 9, respectively.
Figure 6:
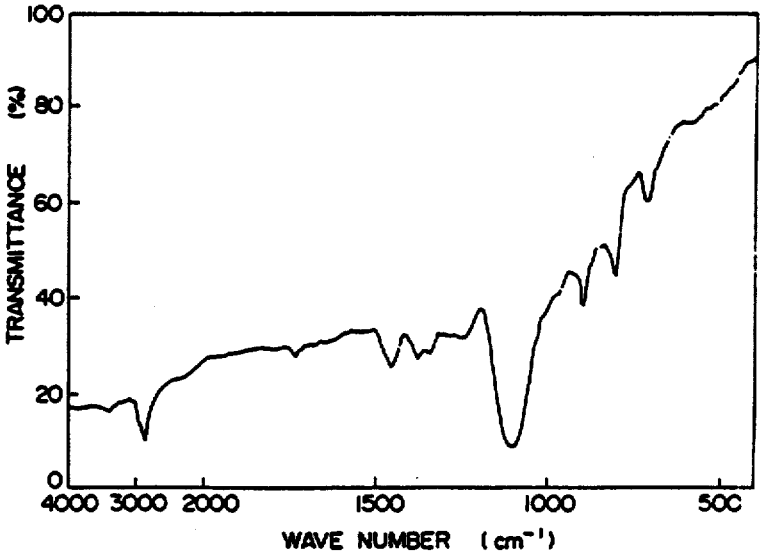
Figure 7:
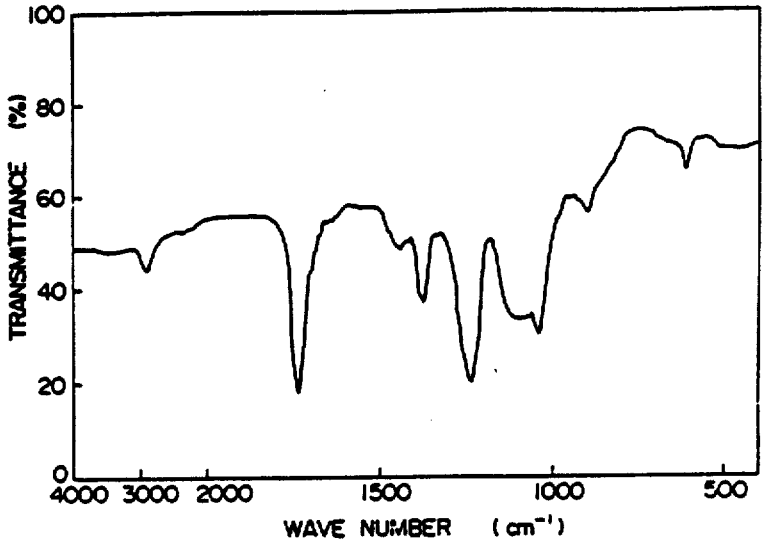
Figure 8:
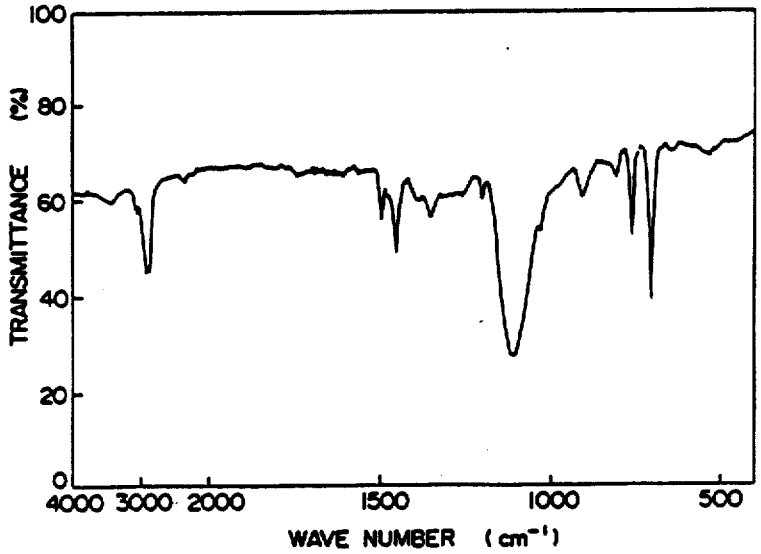
Figure 9:
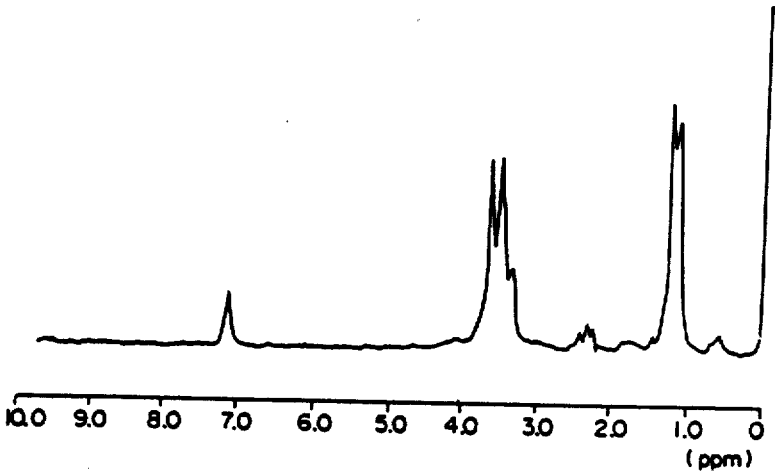
FIGS. 9 and 10 are plots of the $^1H$ NMR spectra of the copolymers obtained in Examples 5 and 6, respectively.

The infrared absorption spectrum of the resulting copolymer is shown in FIG. 4, and its $^1$H NMR spectrum, in FIG. 9.

EXAMPLES 6–9

Figure 10:
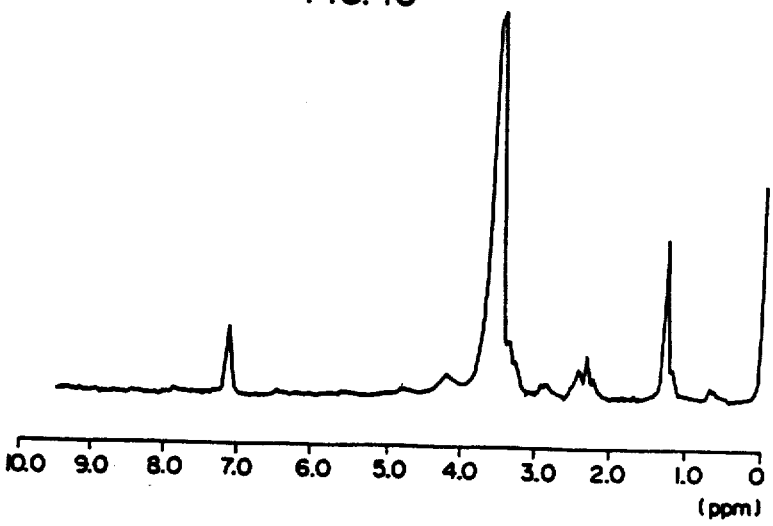

Using the same catalyst as used in Example 5, the same copolymerization as in Example 5 was repeated under the conditions indicated in Table 1. The compositions of the resulting copolymers, determined by $^1$H NMR spectroscopy, are shown in Table 1. The infrared absorption spectra of the copolymers obtained in Examples 6 to 9 are shown in FIGS. 5 to 8, respectively, and the $^1$H NMR spectrum of the copolymer obtained in Example 6, in FIG. 10.

TABLE 1

| Example | 5 | 6 | 7 | 8 | 9 |
|---|---|---|---|---|---|
| Monomer charged (mole %) | | | | | |
| 2,3-Epoxypropyl-2',3'-epoxy-2'-methylpropyl ether | 20 | 30 | 80 | 5 | 40 |
| Propylene oxide | 80 | — | 20 | — | — |
| Epichlorohydrin | — | 70 | — | — | — |
| Glycidyl acetate | — | — | — | 95 | — |
| Styrene oxide | — | — | — | — | 60 |
| Amount of the catalyst (g/mole of monomer) | 0.07 | 0.06 | 0.08 | 0.05 | 0.09 |
| Reaction temperature (°C.) | 40 | 45 | 50 | 50 | 50 |
| Reaction time (hours) | 50 | 50 | 70 | 60 | 70 |
| Copolymer produced | | | | | |
| Yield (%) | 91 | 89 | 65 | 70 | 78 |
| Reduced viscosity, $\eta_{red}$ | 2.48 (*) | 0.82 (**) | 0.15 (*) | 0.35 (*) | 0.78 (*) |
| Composition as monomers (mole %) | | | | | |
| 2,3-Epoxypropyl-2',3'-epoxy-2'-methylpropyl ether | 18 | 21 | 75 | 4 | 31 |
| Propylene oxide | 84 | — | 25 | — | — |
| Epichlorohydrin | — | 79 | — | — | — |
| Glycidyl acetate | — | — | — | 96 | — |
| Styrene oxide | — | — | — | — | 69 |

(*): Measured at 45° C. in a 0.1% benzene solution.
(**): Measured at 80° C. in a 0.1% monochlorobenzene solution.

What is claimed is:

1. A polyether polymer or copolymer with a pendant group of the formula

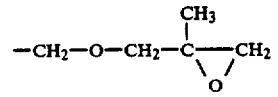

in its molecule, said polymer or copolymer consisting essentially of (1) [1] *5* to 100 mole % of recurring units represented by the following formula (I)

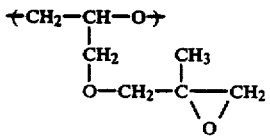

(I)

and (2) [0 to 99] *0 to 95* mole % of at least one type of recurring units represented by the following formula (II)

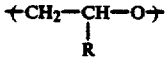

(II)

wherein R represents a member selected from the class consisting of a hydrogen atom, substituted or unsubstituted $C_1$–$C_{18}$ alkyl groups, substituted or unsubstituted $C_2$–$C_{18}$ alkenyl groups, substituted or unsubstituted $C_3$–$C_8$ cycloalkyl groups and substituted or unsubstituted $C_6$–$C_{14}$ aryl groups, and having a reduced viscosity $\eta_{red}$, determined at 45° C. in its 0.1% benzene solution or at 80° C. in its 0.1% monochlorobenzene solution, of at least 0.01.

2. The polyether polymer or copolymer of claim 1 wherein in the definition of R in formula (II), the substituent on the alkyl groups is selected from the class consisting of halogen, $C_1$–$C_{10}$ alkoxy, $C_2$–$C_{10}$ alkoxycarbonyl, $C_2$–$C_{10}$ acyl, $C_1$–$C_{10}$ alkylthio, and optionally substituted $C_6$–$C_{14}$ aryl; the substituent on the alkenyl groups is selected from the class consisting of halogen, $C_1$–$C_{12}$ alkyl, $C_1$–$C_{10}$ alkoxy, $C_2$–$C_{10}$ alkoxycarbonyl, $C_2$–$C_{10}$ acyl and $C_1$–$C_{10}$ alkylthio; the substituent on the cycloalkyl groups is selected from the class consisting of halogen, $C_1$–$C_{12}$ alkyl, $C_1$–$C_{10}$ alkoxy, $C_2$–$C_{10}$ alkoxycarbonyl, $C_2$–$C_{10}$ acyl and $C_1$–$C_{10}$ alkylthio; and the substituent on the aryl groups is selected from the class consisting of halogen, $C_1$–$C_{12}$ alkyl, $C_1$–$C_{10}$ alkoxy, $C_2$–$C_{10}$ alkoxycarbonyl, $C_2$–$C_{10}$ acyl and $C_1$–$C_{10}$ alkylthio.

3. The polyether polymer or copolymer *of claim 1* having a reduced viscosity $\eta_{red}$ of 0.01 to 5.

4. A process for producing the polyether polymer or copolymer of claim 1, which comprises polymerizing 2,3-epoxypropyl-2',3'-epoxy-2'-methylpropyl ether of the following formula (I-a)

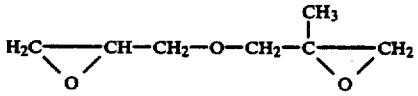

(I-a)

or copolymerizing it with a compound *of* the following formula (III)

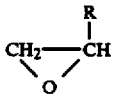

(III)

wherein R represents a member selected from the class consisting of a hydrogen atom, substituted or unsubstituted $C_1$–$C_{18}$ alkyl groups, substituted or unsubstituted $C_2$–$C_{18}$ alkenyl groups, substituted or unsubstituted $C_3$–$C_8$ cycloalkyl groups and substituted or unsubstituted $C_6$–$C_{14}$ aryl groups, in the present of, as a catalyst, a heat-reaction product of (A) an organotin compound and [(b)] (*B*) a complete or partial ester compound of the formula $(HO)_3PO$, said organotin compound (A) being selected from the group consisting of compounds of the following formulae (i) to (iv)

$$R_a^1SnX_{4-a} \quad \text{(i)}$$

wherein $R^1$ represents a $C_1$–$C_{12}$ alkyl group unsubstituted or substituted by a substituent selected from halogen, hydroxy, $C_1$–$C_{10}$ alkoxy and $C_1$–$C_{10}$ alkylthio, a $C_2$–$C_8$ alkenyl group unsubstituted or substituted by a substituent selected from halogen, hydroxy, $C_1$–$C_{10}$ alkoxy, $C_1$–$C_{10}$ alkylthio, and optionally substituted $C_6$–$C_{14}$ aryl, a $C_3$–$C_8$ cycloalkyl group unsubstituted or substituted by a substituent selected from halogen, hydroxy, $C_1$–$C_{12}$ alkyl, $C_1$–$C_{10}$ alkoxy, $C_1$–$C_{10}$ alkylthio and optionally substituted $C_6$–$C_{14}$ aryl, a $C_6$–$C_{14}$ aryl group unsubstituted or substituted by a substituent selected from [halogn] *halogen*, hydroxy, $C_1$–$C_{12}$ alkyl, $C_1$–$C_{10}$ alkoxy, $C_1$–$C_{10}$ alkylthio and optionally substituted $C_6$–$C_{14}$ aryl, or a $C_7$–$C_{18}$ aralkyl group unsubstituted or substituted by a substituent selected from halogen, hydroxy, $C_1$–$C_{12}$ alkyl, $C_1$–$C_{10}$ alkoxy and $C_1$–$C_{10}$ alkylthio; [x] *X* represents an atom or group selected from halogen atoms, $C_1$–$C_{12}$ alkoxy groups, aryloxy groups having [$C_6$–$C_{14}$] *$C_6$–$C_{18}$* aryl *substituents*], [acyloxy] groups having $C_2$–$C_{12}$ acyl *substituents* and residues of partial esters of phosphoric acid; and an is an integer of 1 to 4, provided that when a is an integer of 2 to 4, $R^1$ groups may be identical or different, and when a is 1 or 2, the X's may be identical or different;

$$R_b^1SnO_c \quad \text{(ii)}$$

wherein $R^1$ is as defined with regard to formula (i), b is 1 or 2, and when b is 1, c is 3/2 or when b is 2, c is 1, the compound of formula (ii) may form a complex with the compound of formula (i);

$$R^2\{R_2^1SnOSnR_2^1\}R^2 \quad \text{(iii)}$$

wherein $R^1$ is as defined with regard to formula (i), $R^2$ is as defined with regard to $R^1$ and X, and the two $R^2$ groups may be identical and different; and $$(R_3^2Sn)_dX' \quad \text{(iv)}$$

wherein $R^2$ is the same as defined with regard to formula (iii) provided that at least one of the three $R^2$ groups is a group selected from the groups defined for $R^1$ in formula (i); X' is a member selected from the group consisting of a carbonate group, a phosphorus or oxyacid group, a polybasic carboxylic acid group and a residual moiety of a polyhydric alcohol; and d is a number greater than 1 and corresponds to the basicity of the member X'.

5. The process of claim 4 wherein the complete or partial ester compound (B) is a compound of the following formula $$(R^3O)_3P{=}O$$

wherein $R^3$ represents a member selected from the class consisting of a hydrogen atom, $C_1$–$C_{12}$ alkyl groups $C_2$–$C_{12}$ alkenyl groups and $C_3$–$C_8$ cycloalkyl groups which may be substituted by halogen, and at least one of the $R^3$ groups represents groups other than hydrogen atom.

[6. 2,3-epoxypropyl-2',3'-epoxy-2'-methylpropyl ether of the following formula (I-a)]

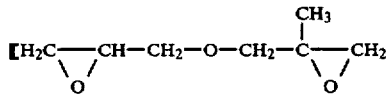

(I-a)]

*7. A polyether copolymer with a pendant group of the formula*

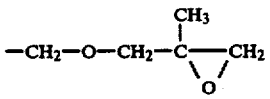

*in its molecule, said copolymer comprising*

*(1) from 1 to 99 mole percent of recurring units of formula (I)*

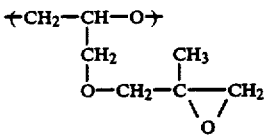

(I)

*and*

*(2) from 1 to 99 mole percent of at least one recurring unit derived from a monoepoxy compound selected from the group consisting of glycidyl acetate, glycidyl propionate, glycidyl benzoate, glycidyl cinnamate and glycidyl naphthonate, said copolymer having a reduced viscosity $\eta_{red}$, determined at 45° C. in its 0.1% benzene solution or at 80° C. in its 0.1% monochlorobenzene solution, of at least 0.01.*

*8. A polyether copolymer with a pendant group of the formula*

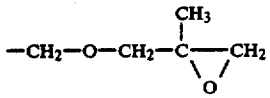

*in its molecule, said copolymer comprising*

*(1) from 1 to 98 mole percent of recurring units of formula (I)*

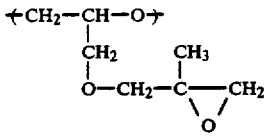

(I)

*(2) 1 to 98 mole percent of at least one type of recurring unit represented by the following formula (II)*

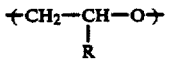

(II)

*wherein R represents a member selected from the class consisting of a hydrogen atom, substituted or unsubstituted $C_1$–$C_{18}$ alkyl groups, substituted or unsubstituted $C_2$–$C_{18}$ alkenyl groups, substituted or unsubstituted $C_3$–$C_8$ cycloalkyl groups and substituted or unsubstituted $C_6$–$C_{14}$ aryl groups, wherein in the definition of R in formula (II), the substituent on the alkyl groups is selected from the class consisting of halogen, $C_1$–$C_{10}$ alkoxy, $C_2$–$C_{10}$ alkoxycarbonyl, $C_2$–$C_{10}$ acyl, $C_1$–$C_{10}$* alkylthio, and optionally substituted $C_6$–$C_{14}$ *aryl; the substituent on the alkenyl groups is selected from the class consisting of halogen, $C_1$–$C_{12}$ alkenyl, $C_1$–$C_{10}$ alkoxy, $C_2$–$C_{10}$ alkoxycarbonyl, $C_2$–$C_{10}$ acyl and $C_1$–$C_{10}$ alkylthio; the substituent on the cycloalkyl groups is selected from the class consisting of halogen, $C_1$–$C_{12}$ alkyl, $C_1$–$C_{10}$ alkoxy, $C_2$–$C_{10}$ alkoxycarbonyl, $C_2$–$C_{10}$ acyl and $C_1$–$C_{10}$ alkylthio; and the substituent on the aryl groups is selected from the class consisting of halogen, $C_1$–$C_{12}$ alkyl, $C_1$–$C_{10}$ alkoxy, $C_2$–$C_{10}$ alkoxycarbonyl, $C_2$–$C_{10}$* acyl and $C_1$–$C_{10}$ *alkylthio, and*

*(3) 1 to 98 mole percent of at least one recurring unit derived from a monoepoxy compound selected from the group consisting of glycidyl acetate, glycidyl propionate, glycidyl benzoate, glycidyl cinnamate and glycidyl napthonate, said copolymer having a reduced viscosity $\eta_{red}$, determined at 45° C. in its 0.1% benzene solution or at 80° C. in its 0.1% monochlorobenzene solution, of at least 0.01.*

* * * * *

UNITED STATES PATENT AND TRADEMARK OFFICE

CERTIFICATE OF CORRECTION

PATENT NO. : Re. 33,367

DATED : October 2, 1990

INVENTOR(S) : Miura, et. al.

It is certified that error appears in the above-identified patent and that said Letters Patent is hereby corrected as shown below:

Col. 16, claim 4, line 28, after "substituents, delete bracket "]";

line 29, before "acyloxy", delete bracket "[", after "acyloxy", delete bracket "]", line 30, delete "an", first occurrence, insert --a--.

Signed and Sealed this

Eighteenth Day of August, 1992

*Attest:*

DOUGLAS B. COMER

*Attesting Officer*

*Acting Commissioner of Patents and Trademarks*